US010480013B2

(12) United States Patent
Muster et al.

(10) Patent No.: US 10,480,013 B2
(45) Date of Patent: Nov. 19, 2019

(54) INFLUENZA VIRUS VECTOR FOR VIROTHERAPY

(71) Applicant: Blue Sky Vaccines GmbH, Vienna (AT)

(72) Inventors: Thomas Muster, Vienna (AT); Markus Wolschek, Vienna (AT)

(73) Assignee: BLUE SKY VACCINES GMBH, Vienna (AT)

( * ) Notice: Subject to any disclaimer, the term of this patent is extended or adjusted under 35 U.S.C. 154(b) by 0 days.

(21) Appl. No.: 16/162,170

(22) Filed: Oct. 16, 2018

(65) Prior Publication Data

US 2019/0032084 A1 Jan. 31, 2019

Related U.S. Application Data

(63) Continuation of application No. 15/031,715, filed as application No. PCT/EP2014/073120 on Oct. 28, 2014, now Pat. No. 10,125,374.

(30) Foreign Application Priority Data

Oct. 28, 2013 (EP) ..................... 13190511

(51) Int. Cl.
*C12N 15/86* (2006.01)
*C07K 14/005* (2006.01)
*C12N 7/00* (2006.01)
*A61K 35/768* (2015.01)
*A61K 38/19* (2006.01)
*A61K 39/395* (2006.01)
*C07K 14/535* (2006.01)
*A61K 39/00* (2006.01)

(52) U.S. Cl.
CPC ............ *C12N 15/86* (2013.01); *A61K 35/768* (2013.01); *A61K 38/193* (2013.01); *A61K 39/395* (2013.01); *C07K 14/005* (2013.01); *C07K 14/535* (2013.01); *C12N 7/00* (2013.01); *A61K 2039/505* (2013.01); *C12N 2760/16122* (2013.01); *C12N 2760/16132* (2013.01); *C12N 2760/16143* (2013.01); *C12N 2760/16145* (2013.01); *C12N 2760/16151* (2013.01); *C12N 2760/16162* (2013.01)

(58) Field of Classification Search
None
See application file for complete search history.

(56) References Cited

U.S. PATENT DOCUMENTS

| 2009/0010962 A1* | 1/2009 | Palese | A61K 39/145 424/199.1 |
| 2010/0136052 A1* | 6/2010 | Wolschek | C07K 14/005 424/206.1 |

FOREIGN PATENT DOCUMENTS

CN 1993140 7/2007

OTHER PUBLICATIONS

Wressnigg et al., Influenza B mutant viruses with truncated NS1 proteins grow efficiently in Vero cells and are immunogenic in mice, 2009, JOurnal of General Virology, vol. 90, pp. 366-374.*
Pachler and Vlasak, Influenza C virus NS1 protein counteracts RIG-I-mediated IFN signalling, 2011, Virology Journal, vol. 8, No. 48.*
Okazaki and Honjo, PD-1 and PD-1 ligands: from discovery to clinical application, 2007, International Immunology, vol. 19, No. 7, pp. 813-824.*
First Office Action, corresponding Chinese Application No. 201480071322.3, dated Feb. 11, 2019.

* cited by examiner

*Primary Examiner* — Benjamin P Blumel
(74) *Attorney, Agent, or Firm* — Loza & Loza, LLP; Michael F. Fedrick

(57) ABSTRACT

The present invention provides a recombinant influenza virus vector comprising an NS gene encoding a truncated NS1 protein of at least 73 and up to 122 amino acids of the N-terminus of the respective wild type NS1 protein, wherein the vector replicates in IFN-sensitive tumor cells and does not replicate in normal, non-tumor cells, and expresses a heterologous immunostimulatory polypeptide. The invention further provides a pharmaceutical composition containing the influenza virus vector, its use for the treatment of cancer patients and methods for producing the influenza virus vaccine.

14 Claims, 5 Drawing Sheets

Figure 3:
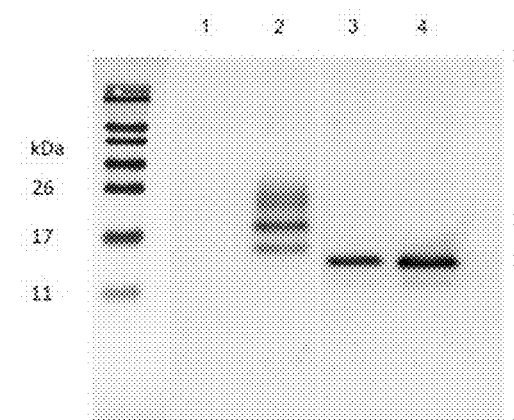

Specification includes a Sequence Listing.

Fig. 1 deINS106-2A-mGM-CSF

1259 bp

Fig. 2 deINS106-2A-GFP

1544 bp

Fig. 6: (SEQ ID NO. 2)

AGCAAAAGCAGGGTGACAAAGACATAATGGATCCAAACACTGTGTCAAGCTTTC
AGGTAGATTGCTTTCTTTGGCATGTCCGCAAACGAGTTGCAGACCAAGAACTAGG
TGATGCCCCATTCCTTGATCGGCTTCGCCGAGATCAGAAATCCCTAAGAGGAAGG
GGCAGCACCCTCGGTCTGGACATCGAGACAGCCACACGTGCTGGAAAGCAGATA
GTGGAGCGGATTCTGAAAGAAGAATCCGATGAGGCACTTAAAATGACCATGGCC
TCTGTACCTGCGTCGCGTTACCTAACTGACATGACTCTTGAGGAAATGTCAAGGG
ACTGGTCCATGCTCATAGGGGGAAATTTCGATCTTCTAAAACTTGCAGGGGATGT
GGAATCAAATCCAGGACCAATGAAGACAGATACACTTCTTCTTTGGGTGCTGCTT
TTGTGGGTTCCAAGATCACATGGGGCACCAACAAGATCACCAATTACAGTGACAA
GACCATGGAAACACGTGGAAGCAATCAAAGAAGCACTTAATCTGCTTGATGATA
TGCCAGTGACACTGAATGAAGAGGTGGAAGTGGTGTCAAATGAGTTCAGCTTCA
AAAAACTGACATGCGTGCAGACAAGACTGAAAATTTTCGAACAAGGACTGAGGG
GAAACTTCACAAAACTTAAAGGGGCACTGAATATGACAGCAAGCTATTATCAAA
CATACTGCCCACCAACACCAGAAACAGATTGCGAAACACAAGTGACAACATACG
CAGATTTCATCGACAGCCTTAAAACATTCCTGACAGATATCCCATTCGAGTGCAA
AAAACCAGGGCAGAAGTGATAATAAGCGGCCGCCCAAGCAGAAAGTGGTACTAA
CCTTCTTCTCTTTCTTCTCCTGACAGGACATACTGCTGAGGATGTCAAAAATGCAG
TTGGAGTCCTCATCGGGGGACTTGAATGGAATGATAACACAGTTCGAGTCTCTGA
AACTCTACAGAGATTCGCTTGGAGAAGCAGTAATGAGAATGGGAGACCTCCACT
CACTCCAAAACAGAAACGAGAAATGGCGGGAACAATTAGGTCAGAAGTTTGAAG
AAATAAGATGGTTGATTGAAGAAGTGAGACACAAACTGAAGATAACAGAGAATA
GTTTTGAGCAAATAACATTTATGCAAGCCTTACATCTATTGCTTGAAGTGGAGCA
AGAGATAAGAACTTTCTCGTTTCAGCTTATTTAATAATAAAAAACACCCTTGTTTC
TACT

Fig. 7: (SEQ ID NO. 3)

MDPNTVSSFQVDCFLWHVRKRVADQELGDAPFLDRLRRDQKSLRGRGSTLGLD
IETATRAGKQIVERILKEESDEALKMTMASVPASRYLTDMTLEEMSRDWSMLIG
<u>GNFDLLKLAGD</u>VESNPGP*MKTDTLLLWVLLLWVPRSHGAPTRSPITVTRPWKHVEAIKEA*
*LNLLDDMPVTLNEEVEVVSNEFSFKKLTCVQTRLKIFEQGLRGNFTKLKGALNMTASYYQT*
*YCPPTPETDCETQVTTYADFIDSLKTFLTDIPFECKKPGQK*

Fig. 8: (SEQ ID NO. 4)

AGCAAAAGCAGGGTGACAAAGACATAATGGATCCAAACACTGTGTCAAGCTTTC
AGGTAGATTGCTTTCTTTGGCATGTCCGCAAACGAGTTGCAGACCAAGAACTAGG
TGATGCCCCATTCCTTGATCGGCTTCGCCGAGATCAGAAATCCCTAAGAGGAAGG
GGCAGCACCCTCGGTCTGGACATCGAGACAGCCACACGTGCTGGAAAGCAGATA
GTGGAGCGGATTCTGAAAGAAGAATCCGATGAGGCACTTAAAATGACCATGGCC
TCTGTACCTGCGTCGCGTTACCTAACTGACATGACTCTTGAGGAAATGTCAAGGG
ACTGGTCCATGCTCATAGGGGGAAATTTCGATCTTCTAAAACTTGCAGGGGATGT
GGAATCAAATCCAGGACCAATGGCATCAAAGGGGAAGAACTTTTTACAGGGGT
GGTGCCAATACTTGTGGAACTTGATGGGGATGTGAATGGACACAAATTCTCAGTT
AGCGGAGAGGGAGAAGGAGATGCAACATACGGAAAACTTACACTGAAATTCATC
TGCACAACTGGAAAACTTCCAGTTCCATGGCCAACACTTGTGACAACACTTTGTT
ATGGGGTGCAATGCTTCTCAAGATACCCAGATCATATGAAGAGGCACGATTTCTT
CAAATCAGCAATGCCAGAGGGATACGTGCAAGAGAACAATATTCTTCAAAGA
CGACGGGAACTACAAGACAAGAGCAGAAGTGAAATTCGAGGGGGATACACTTGT
GAATAGAATAGAACTGAAGGGAATCGACTTCAAAGAGGATGGAAATATTCTGGG
ACACAAGCTCGAGTACAACTACAATAGCCATAATGTGTACATCATGGCCGACAA
GCAGAAAAACGGAATCAAAGTGAACTTCAAGACTAGGCATAATATTGAGGATGG
ATCAGTGCAACTGGCAGATCATTATCAACAAAACACACCAATTGGAGATGGACC
AGTGCTTCTGCCAGATAATCATTACCTTTCAACACAGTCAGCACTGAGCAAAGAT
CCAAATGAGAAAAGGGATCATATGGTGCTGCTTGAATTTGTGACAGCAGCTGGA
ATTACACATGGAATGGATGAGCTGTACAACTGATAATAAGCGGCCGCCCAAGCA
GAAAGTGGTACTAACCTTCTTCTCTTTCTTCTCCTGACAGGACATACTGCTGAGGA
TGTCAAAAATGCAGTTGGAGTCCTCATCGGGGACTTGAATGGAATGATAACACA
GTTCGAGTCTCTGAAACTCTACAGAGATTCGCTTGGAGAAGCAGTAATGAGAATG
GGAGACCTCCACTCACTCCAAAACAGAAACGAGAAATGGCGGGAACAATTAGGT
CAGAAGTTTGAAGAAATAAGATGGTTGATTGAAGAAGTGAGACACAAACTGAAG
ATAACAGAATAGTTTTGAGCAAATAACATTTATGCAAGCCTTACATCTATTGC
TTGAAGTGGAGCAAGAGATAAGAACTTTCTCGTTTCAGCTTATTTAATAATAAAA
AACACCCTTGTTTCTACT

Fig. 9: (SEQ ID NO. 5)

**MDPNTVSSFQVDCFLWHVRKRVADQELGDAPFLDRLRRDQKSLRGRGSTLGLD
IETATRAGKQIVERILKEESDEALKMTMASVPASRYLTDMTLEEMSRDWSMLIG
GNFDLLKLAGDVESNPGP**MASKGEELFTGVVPILVELDGDVNGHKFSVSGEGEGDATYG
KLTLKFICTTGKLPVPWPTLVTTLCYGVQCFSRYPDHMKRHDFFKSAMPEGYVQERTIFF
KDDGNYKTRAEVKFEGDTLVNRIELKGIDFKEDGNILGHKLEYNYNSHNVYIMADKQKNG
IKVNFKTRHNIEDGSVQLADHYQQNTPIGDGPVLLPDNHYLSTQSALSKDPNEKRDHMVL
LEFVTAAGITHGMDELYN

Fig. 10 (SEQ ID NO. 1)
MDPNTVSSFQVDCFLWHVRKRVADQELGDAPFLDRLRRDQKSLRGRGSTLGLDIET

ATRAGKQIVERILKEESDEALKMTMASVPASRYLTDMTLEEMSRDWSMLIPKQKVA

GPLCIRMDQAIMDKNIILKANFSVIFDRLETLILLRAFTEEGAIVGEISPLPSLPGHTAED

VKNAVGVLIGGLEWNDNTVRVSETLQRFAWRSSNENGRPPLTPKQKREMAGTIRSE

V

SEQUENCE LISTING

```
<160> NUMBER OF SEQ ID NOS: 10

<210> SEQ ID NO 1
<211> LENGTH: 230
<212> TYPE: PRT
<213> ORGANISM: Artificial Sequence
<220> FEATURE:
<223> OTHER INFORMATION: wild-type PR8 NS1

<400> SEQUENCE: 1
```

```
Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Ala Ser Val Pro Ala Ser Arg Tyr Leu Thr Asp Met Thr Leu Glu
                85                  90                  95

Glu Met Ser Arg Asp Trp Ser Met Leu Ile Pro Lys Gln Lys Val Ala
            100                 105                 110

Gly Pro Leu Cys Ile Arg Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Ala Glu Asp Val Lys Asn
                165                 170                 175

Ala Val Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
        195                 200                 205

Asn Gly Arg Pro Pro Leu Thr Pro Lys Gln Lys Arg Glu Met Ala Gly
    210                 215                 220

Thr Ile Arg Ser Glu Val
225                 230

<210> SEQ ID NO 2
<211> LENGTH: 1259
<212> TYPE: DNA
<213> ORGANISM: Artificial Sequence
<220> FEATURE:
<223> OTHER INFORMATION: delNS106-2A-mGM-CSF

<400> SEQUENCE: 2
agcaaaagca gggtgacaaa gacataatgg atccaaacac tgtgtcaagc tttcaggtag      60
attgctttct ttggcatgtc cgcaaacgag ttgcagacca agaactaggt gatgccccat     120
tccttgatcg gcttcgccga gatcagaaat ccctaagagg aagggcagc accctcggtc     180 tggacatcga gacagccaca cgtgctggaa agcagatagt ggagcggatt ctgaaagaag     240
aatccgatga ggcacttaaa atgaccatgg cctctgtacc tgcgtcgcgt tacctaactg     300
acatgactct tgaggaaatg tcaagggact ggtccatgct cataggggga aatttcgatc     360
ttctaaaact tgcaggggat gtggaatcaa atccaggacc aatgaagaca gatacacttc     420
ttctttgggt gctgcttttg tgggttccaa gatcacatgg ggcaccaaca agatcaccaa     480
ttacagtgac aagaccatgg aaacacgtgg aagcaatcaa agaagcactt aatctgcttg     540
atgatatgcc agtgacactg aatgaagagg tggaagtggt gtcaaatgag ttcagcttca     600
aaaaactgac atgcgtgcag acaagactga aaatttcga caaggactg aggggaaact     660 tcacaaaact taaggggca ctgaatatga cagcaagcta ttatcaaaca tactgcccac     720
```

```
caacaccaga aacagattgc gaaacacaag tgacaacata cgcagatttc atcgacagcc    780
ttaaaacatt cctgacagat atcccattcg agtgcaaaaa accagggcag aagtgataat    840
aagcggccgc ccaagcagaa agtggtacta accttcttct ctttcttctc ctgacaggac    900
atactgctga ggatgtcaaa aatgcagttg gagtcctcat cggggggactt gaatggaatg    960 ataacacagt tcgagtctct gaaactctac agagattcgc ttggagaagc agtaatgaga    1020
atgggagacc tccactcact ccaaaacaga acgagaaat ggcgggaaca attaggtcag     1080
aagtttgaag aaataagatg gttgattgaa gaagtgagac acaaactgaa gataacagag    1140
aatagttttg agcaaataac atttatgcaa gccttacatc tattgcttga agtggagcaa    1200
gagataagaa ctttctcgtt tcagcttatt taataataaa aaacacccct gtttctact    1259
```

```
<210> SEQ ID NO 3
<211> LENGTH: 269
<212> TYPE: PRT
<213> ORGANISM: Artificial Sequence
<220> FEATURE:
<223> OTHER INFORMATION: NS106-2A-mGM-CSF

<400> SEQUENCE: 3
```

Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Ala Ser Val Pro Ala Ser Arg Tyr Leu Thr Asp Met Thr Leu Glu
                85                  90                  95

Glu Met Ser Arg Asp Trp Ser Met Leu Ile Gly Gly Asn Phe Asp Leu
            100                 105                 110

Leu Lys Leu Ala Gly Asp Val Glu Ser Asn Pro Gly Pro Met Lys Thr
        115                 120                 125

Asp Thr Leu Leu Leu Trp Val Leu Leu Leu Trp Val Pro Arg Ser His
    130                 135                 140

Gly Ala Pro Thr Arg Ser Pro Ile Thr Val Thr Arg Pro Trp Lys His
145                 150                 155                 160

Val Glu Ala Ile Lys Glu Ala Leu Asn Leu Leu Asp Asp Met Pro Val
                165                 170                 175

Thr Leu Asn Glu Glu Val Glu Val Val Ser Asn Glu Phe Ser Phe Lys
            180                 185                 190

Lys Leu Thr Cys Val Gln Thr Arg Leu Lys Ile Phe Glu Gln Gly Leu
        195                 200                 205

Arg Gly Asn Phe Thr Lys Leu Lys Gly Ala Leu Asn Met Thr Ala Ser
    210                 215                 220

Tyr Tyr Gln Thr Tyr Cys Pro Pro Thr Pro Glu Thr Asp Cys Glu Thr
225                 230                 235                 240

Gln Val Thr Thr Tyr Ala Asp Phe Ile Asp Ser Leu Lys Thr Phe Leu
                245                 250                 255

Thr Asp Ile Pro Phe Glu Cys Lys Lys Pro Gly Gln Lys
            260                 265

<210> SEQ ID NO 4
<211> LENGTH: 1544
<212> TYPE: DNA
<213> ORGANISM: Artificial Sequence
<220> FEATURE:
<223> OTHER INFORMATION: delNS106-2A-GFP

<400> SEQUENCE: 4

```
agcaaaagca gggtgacaaa gacataatgg atccaaacac tgtgtcaagc tttcaggtag      60
attgctttct ttggcatgtc cgcaaacgag ttgcagacca gaactaggt gatgccccat      120
tccttgatcg gcttcgccga gatcagaaat ccctaagagg aaggggcagc accctcggtc     180
tggacatcga gacagccaca cgtgctggaa agcagatagt ggagcggatt ctgaaagaag     240
aatccgatga ggcacttaaa atgaccatgg cctctgtacc tgcgtcgcgt tacctaactg     300
acatgactct tgaggaaatg tcaagggact ggtccatgct catagggggga aatttcgatc     360
ttctaaaact gcaggggat gtggaatcaa atccaggacc aatggcatca aaagggaag      420
aacttttttac aggggtggtg ccaatacttg tggaacttga tggggatgtg aatggacaca     480
aattctcagt tagcggagag ggagaaggag atgcaacata cggaaaactt acactgaaat     540
tcatctgcac aactggaaaa cttccagttc catggccaac acttgtgaca cactttgtt      600
atggggtgca atgcttctca agatacccag atcatatgaa gaggcacgat ttcttcaaat     660
cagcaatgcc agagggatac gtgcaagaga gaacaatatt cttcaaagac gacgggaact     720
acaagacaag agcagaagtg aaattcgagg gggatacact tgtgaataga atagaactga     780
agggaatcga cttcaaagag gatggaaata ttctgggaca caagctcgag tacaactaca     840
atagccataa tgtgtacatc atggccgaca gcagaaaaa cggaatcaaa gtgaacttca     900
agactaggca taatattgag gatggatcag tgcaactggc agatcattat caacaaaaca     960
caccaattgg agatggacca gtgcttctgc cagataatca ttacctttca acacagtcag     1020
cactgagcaa agatccaaat gagaaaaggg atcatatggt gctgcttgaa tttgtgacag     1080
cagctggaat tacacatgga atggatgagc tgtacaactg ataataagcg gccgcccaag     1140
cagaaagtgg tactaacctt cttctctttc ttctcctgac aggacatact gctgaggatg     1200
tcaaaaatgc agttggagtc ctcatcgggg gacttgaatg gaatgataac acagttcgag     1260
tctctgaaac tctacagaga ttcgcttgga aagcagtaa tgagaatggg agacctccac     1320
tcactccaaa acagaaacga gaaatggcgg gaacaattag gtcagaagtt tgaagaaata     1380
agatggttga ttgaagaagt gagacacaaa ctgaagataa cagagaatag ttttgagcaa     1440
ataacattta tgcaagcctt acatctattg cttgaagtgg agcaagagat aagaactttc     1500
tcgtttcagc ttatttaata ataaaaaaca cccttgtttc tact                     1544
```

<210> SEQ ID NO 5
<211> LENGTH: 364
<212> TYPE: PRT
<213> ORGANISM: Artificial Sequence
<220> FEATURE:
<223> OTHER INFORMATION: NS106-2A-mGM-CSF

<400> SEQUENCE: 5

```
Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
            20                  25                  30
```

-continued

```
Leu Asp Arg Leu Arg Arg Asp Gln Lys Ser Leu Arg Gly Arg Gly Ser
            35                  40                  45

Thr Leu Gly Leu Asp Ile Glu Thr Ala Thr Arg Ala Gly Lys Gln Ile
 50                  55                  60

Val Glu Arg Ile Leu Lys Glu Glu Ser Asp Glu Ala Leu Lys Met Thr
 65                  70                  75                  80

Met Ala Ser Val Pro Ala Ser Arg Tyr Leu Thr Asp Met Thr Leu Glu
                 85                  90                  95

Glu Met Ser Arg Asp Trp Ser Met Leu Ile Gly Asn Phe Asp Leu
            100                 105                 110

Leu Lys Leu Ala Gly Asp Val Glu Ser Asn Pro Gly Pro Met Ala Ser
            115                 120                 125

Lys Gly Glu Glu Leu Phe Thr Gly Val Val Pro Ile Leu Val Glu Leu
            130                 135                 140

Asp Gly Asp Val Asn Gly His Lys Phe Ser Val Ser Gly Glu Gly Glu
145                 150                 155                 160

Gly Asp Ala Thr Tyr Gly Lys Leu Thr Leu Lys Phe Ile Cys Thr Thr
                165                 170                 175

Gly Lys Leu Pro Val Pro Trp Pro Thr Leu Val Thr Thr Leu Cys Tyr
            180                 185                 190

Gly Val Gln Cys Phe Ser Arg Tyr Pro Asp His Met Lys Arg His Asp
            195                 200                 205

Phe Phe Lys Ser Ala Met Pro Glu Gly Tyr Val Gln Glu Arg Thr Ile
210                 215                 220

Phe Phe Lys Asp Asp Gly Asn Tyr Lys Thr Arg Ala Glu Val Lys Phe
225                 230                 235                 240

Glu Gly Asp Thr Leu Val Asn Arg Ile Glu Leu Lys Gly Ile Asp Phe
                245                 250                 255

Lys Glu Asp Gly Asn Ile Leu Gly His Lys Leu Glu Tyr Asn Tyr Asn
            260                 265                 270

Ser His Asn Val Tyr Ile Met Ala Asp Lys Gln Lys Asn Gly Ile Lys
            275                 280                 285

Val Asn Phe Lys Thr Arg His Asn Ile Glu Asp Gly Ser Val Gln Leu
            290                 295                 300

Ala Asp His Tyr Gln Gln Asn Thr Pro Ile Gly Asp Gly Pro Val Leu
305                 310                 315                 320

Leu Pro Asp Asn His Tyr Leu Ser Thr Gln Ser Ala Leu Ser Lys Asp
                325                 330                 335

Pro Asn Glu Lys Arg Asp His Met Val Leu Leu Glu Phe Val Thr Ala
            340                 345                 350

Ala Gly Ile Thr His Gly Met Asp Glu Leu Tyr Asn
            355                 360
```

<210> SEQ ID NO 6
<211> LENGTH: 12
<212> TYPE: DNA
<213> ORGANISM: Artificial Sequence
<220> FEATURE:
<223> OTHER INFORMATION: Primer

<400> SEQUENCE: 6
agcaaaagca gg                                                      12

<210> SEQ ID NO 7
<211> LENGTH: 21
<212> TYPE: DNA

```
<213> ORGANISM: Artificial Sequence
<220> FEATURE:
<223> OTHER INFORMATION: Primer

<400> SEQUENCE: 7
agcaaaagca gggtgacaaa g                                                  21

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
ctcttgctcc acttcaagc                                                     19

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
cttaaacttg caggagatgt g                                                  21

<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10
gatgaggact ccaactgc                                                      18
```

INFLUENZA VIRUS VECTOR FOR VIROTHERAPY

CROSS-REFERENCE TO RELATED APPLICATIONS

This application is a continuation of U.S. patent application Ser. No. 15/031,715, filed on Apr. 22, 2016 and entitled NOVEL INFLUENZA VIRUS VECTOR FOR VIROTHERAPY, which is the U.S. national stage of International Patent Application No. PCT/EP2014/073120, filed on Oct. 28, 2014, which claims the benefit of priority under 35 U.S.C. § 119 from European Patent Application No. 13190511.9, filed on Oct. 28, 2013. The disclosures of the foregoing applications are incorporated herein by reference in their entirety.

SEQUENCE LISTING

The entire content of a Sequence Listing titled "Sequence_ Listing.txt," created on Apr. 13, 2016 and having a size of 12 kilobytes, which has been submitted in electronic form in connection with the present application, is hereby incorporated by reference herein in its entirety.

FIELD OF THE INVENTION

The present invention provides a novel recombinant influenza virus vector comprising an NS gene encoding a truncated NS1 protein of up to 123 amino acids, specifically up to 117 amino acids of the N-terminus of the respective wild type NS1 protein, wherein said vector replicates efficiently in IFN-sensitive tumor cells while being attenuated and replication-deficient in normal, non-tumor cells, and expresses a heterologous immunostimulatory polypetide.

The invention specifically is useful in the field of therapeutic cancer vaccine and relates to therapeutic vaccine vectors, more specifically to vectors derived from genetically modified influenza A virus strains.

BACKGROUND

Advanced metastatic cancers are largely incurable since cancers have found multiple different ways to usurp signalling pathways to gain a growth advantage. Therefore it is unlikely that pharmacological attack on a single molecular target will significantly impact the long-term progression of the malignancy (Jones et al., 2008, Science 321: 1801-1806). Moreover, tumor cells become very heterogeneous as they evolve under the selective pressure of their microenvironment (Subarsky, P and Hill, R P, 2003, Clin Exp Metastasis 20: 237-250).

While our immune system has the capacity to rapidly respond and has the potential to recognize the antigenic variations presented by tumor cells (Cheever et al., 2009, Clin Cancer Res 15: 5323-5337), in particular advanced tumors are highly immunosuppressive. The ability to create an immunosuppressive environment permits the cancer cells to avoid detection by the immune system. They inhibit the maturation of local professional antigen-presenting cells by secreting cytokines and other molecules that inhibit the expression of costimulatory molecules, essential for the expansion of T cells (Strobl, H and Knapp, W., 1999, Microbes Infect 1: 1283-1299; Fiorentino, D F et al., 1991, J Immunol 146: 3444-3451). Tumors also directly inhibit T cells and instead of costimulatory molecules, many tumors express coinhibitory molecules. Some tumors may not express inhibitory molecules themselves, but recruit inhibitory cell types such as T-regulatory cells do. The fact that advanced tumors are highly immunosuppressive demonstrates the importance of the immune system in this context. Besides creating an immunosuppressive environment, tumor cells escape the immune system by poor or even lack of presentation of tumor antigens to effector T cells (Maeurer, M J, et al., 1996, Clin Cancer Res 2: 641-652).

All these properties make cancer a complex disease and a challenging one to treat.

Viruses have two important properties to overcome both heterogeneity and immune escape mechanisms of the tumor:

First, viruses can take advantage of the same pathways that tumor cells activate during malignant progression, for their own growth—resulting in destruction of the tumor (Bergmann M, et al., 2001, Cancer Res., 61: 8188-93; Muster T, et al., 2004, Int J Cancer 110: 15-21; Kim, et al., 2010, Oncogene 29: 3990-3996; Mansour M, et al., 2011. J. Virol. 85: 6015-6023).

Second, viruses are capable to activate both innate and adaptive immune responses against the tumor (Prestwich, R J et al., 2009, Clin Cancer Res 15: 4374-4381; Kim et al., 2010; Immunol. Letters, 134(1), November 30; 134(1):47-54, Ramirez et al., 2010, Discov Med 10: 387-393). Importantly, these inherent immunogenic properties of the virus can be further enhanced by introducing immunostimulatory molecules such as cytokines and tumor associated antigens into the virus.

Viruses as "dual mechanism cancer therapies"—both killing cancer cells and inducing anti-tumor immune response—represent one of the most promising new strategies to treat cancer. Virotherapy reduces the bulk of the tumor and modulate the immunosuppressive environment by activation of toll-like receptors and expression of transgenic immune enhancing cytokines. The immune enhancing cytokines activate and stimulate cancer-specific T-cells, which subsequently eliminate residual and metastatic tumor cells that may be resistant to viral lysis. It has become increasingly clear that the innate and adaptive immune responses triggered by oncolytic viruses in an otherwise immunosuppressive environment of a tumor are critical components of the clinical benefit of these therapeutics. The potential to modulate the immune suppressive environment of the tumor is due to the inherent ability of many viruses to be strong inducers of T-cell mediated immune responses: T-cell numbers in the body are maintained at a homeostatic steady state unless disturbed by infection or lymphopenia. Inflammatory responses to most pathogens result from the recognition of pathogen-associated molecular patterns by receptors on innate immune system cells like dendritic cells (DC) and natural killer (NK) cells. For example, toll-like receptors recognize structures unique to pathogens such as double stranded RNAs, and toll-like receptor ligation signals the production of cytokines and chemokines that recruit and induce expansion of T cells specific for the infecting pathogen. In contrast to tumor cells which do not express pathogen-associated molecular patterns and therefore fail to activate the innate immune system, most viruses encode several toll-like receptor ligands that effectively activate innate immunity. In particular RNA viruses are strong inducers of innate immune responses since they generate double stranded RNA during replication which effectively interacts with toll-like receptors (Diebold et al., 2003, Nature 424: 324-8.; Shi, Z, et al., 2011, J Biol Chem 286: 4517-4524; Ahmed, M, et al., 2009, J Virol 83: 2962-2975; Appledorn et al., 2011, Clin Vaccine Immunol 18: 150-160). As a consequence, upon intratumoral delivery the mere presence of a virus within a tumor can act as a "danger signal" to alert and activate the immune system (Gallucci and Matzinger, 2001, Curr Opin Immunol 13: 114-119).

The oncolytic properties of influenza virus with deletions in the NS1 gene and their lack of replication in normal cells were reported. However, the mutants were limited to tumor cells with defects in the interferon pathway (WO2009/007244A2). The mutants described in WO2009/007244A2 are characterized by a complete lack of a functional RNA-binding site.

Other mutants not limited to tumor cells with defects in the IFN pathway were only slightly attenuated (WO2004111249A2). Effective replication and expression of the heterologous gene by the vector described in WO2004111249A2, was reported not to be limited in IFN competent cells or sensitive to the effects of IFN.

However, the vector of WO2004111249A2 also grows effectively in normal (IFN competent) cells and animals. Importantly, in contrast to the vector described in the present invention it does not have an optimal conditional replication phenotype. Therefore it does not fulfil an important requirement for a virotherapy approach.

The influenza virion consists of an internal ribonucleoprotein core (a helical nucleocapsid) containing the single-stranded RNA genome, and an outer lipoprotein envelope lined inside by a matrix protein (M1). The segmented genome of influenza A and B virus consists of eight segments, seven for influenza C, of linear, negative polarity, single-stranded RNAs which encode eleven, some influenza A strains ten, polypeptides, including the RNA-dependent RNA polymerase proteins (PB2, PB1 and PA) and nucleoprotein (NP) which form the nucleocapsid; the matrix membrane proteins (M1, M2 or BM2 for influenza B, respectively); two surface glycoproteins which project from the lipid containing envelope: hemagglutinin (HA) and neuraminidase (NA); the nonstructural protein (NS1) and the nuclear export protein (NEP). Influenza B viruses encode also NB, a membrane protein which might have ion channel activity and most influenza A strains also encode an eleventh protein (PB1-F2) believed to have proapoptotic properties. Transcription and replication of the genome takes place in the nucleus and assembly occurs via budding on the plasma membrane. The viruses can reassort genes during mixed infections. Influenza virus adsorbs via HA to sialyloligosaccharides in cell membrane glycoproteins and glycolipids. Following endocytosis of the virion, a conformational change in the HA molecule occurs within the cellular endosome which facilitates membrane fusion, thus triggering uncoating. The nucleocapsid migrates to the nucleus where viral mRNA is transcribed. Viral mRNA is transcribed and processed by a unique mechanism in which viral endonuclease cleaves the capped 5'-terminus from cellular heterologous mRNAs which then serve as primers for transcription from viral RNA templates by the viral transcriptase. Transcripts terminate at sites 15 to 22 bases from the ends of their templates, where oligo(U) sequences act as signals for the addition of poly(A) tracts. Of the eight viral RNA molecules of influenza A virus so produced, six are monocistronic messages that are translated directly into the proteins representing HA, NA, NP and the viral polymerase proteins, PB2, PB1 and PA. The other two transcripts undergo splicing, each yielding two mRNAs which are translated in different reading frames to produce M1, M2, NS1 and NEP. In most of influenza A viruses, segment 2 also encodes for a second protein (PB1-F2), expressed from an overlapping reading frame. In other words, the eight viral RNA segments code for eleven proteins: nine structural and 2 non-structural (NS1, PB1-F2) proteins.

There is a constant and unmet need for virotherapy which effectively destroys a wide variety of tumor cells and tumors but is sufficiently attenuated in normal cells or tissues.

SHORT DESCRIPTION OF THE INVENTION

The problem is solved by the present invention.

A virus is provided which is not limited to the treatment of tumor cells with defects in the IFN pathway. This virus has not only retained the replication capacity in IFN-sensitive tumor cells but is also sufficiently attenuated and replication-deficient in normal cells.

Besides common advantages among viruses used for virotherapy such as strong immunostimulatory properties through induction of type I IFN and chemokines, and the specificity of the virus for cancer cells due to their defects in antiviral and apoptotic pathways a virotherapy is provided by the present invention which is based on influenza virus that has features, which allow to fully exploit the potential of virotherapy against cancer by combining the functional characteristics of:

(i) Construction of influenza viruses with different deletions in their NS1 protein. The length of the NS1 protein inversely correlates with the level of attenuation. This feature of the delNS1 virus allows the choice of length of the NS1 protein, which is associated with efficient tumor destruction but is still attenuated enough in the host to allow a safe application of the virus. In particular, in contrast to other approaches which are dependent on tumor cells defective in the interferon pathway NS mutants are defined which allow also to target cancer cells which do not have a defect in the interferon pathway.

(ii) For influenza viruses, multiple serologically defined subtypes exist. In this invention different subtypes of the oncolytic influenza virus can be obtained by exchanging the antigenic surface-glycoproteins of the virus. The availability of such variants facilitates effective repeated administration. Importantly, the availability of different influenza virus types (influenza A, B and C) permits not only to circumvent B-cell mediated but also T-cell mediated immune responses to the vector.

The mutant of the invention has an optimal conditional replicating phenotype for virotherapy against cancer. Specifically, while attenuation in normal cells is a pre-requisite for a virotherapy approach, this mutant is not limited to be used against tumor cells that are defective in the interferon pathway. It has the ability to replicate in interferon-sensitive and interferon-resistant tumor cells. Importantly, replication of the vector is essential for the inserted cytokine to be expressed. Inducing cytokines in the tumor tissue is beneficial in activating innate and adaptive immune responses and replication of the virus allows expression of its own as well as heterologous genes and to directly destroy cancer cells by lyses.

The inventive virus vector for virotherapy has the optimal balance between attenuation in normal cells and has the ability to replicate and express foreign genes effectively also in IFN-sensitive (IFN-competent) tumor cells, and is characterized by comprising an NS1 protein which (i) retains functional RNA binding site (aa 1-73) and (ii) lacks essential parts of the effector domain (aa 123-207, specifically 117-207) according to the amino acid numbering of the wild-type sequence (SEQ ID NO. 1).

The present invention thus provides a recombinant influenza virus vector comprising an NS gene encoding a truncated NS1 protein of up to 122 and not more than 122 amino acids, specifically up to 117 amino acids, of the N-terminus of the respective wild type NS1 protein and a heterologous, non viral sequence encoding an immunostimulatory polypeptide, wherein said vector
  (i) replicates in IFN-sensitive tumor cells and does not replicate in normal, non-tumor cells, and
  (ii) expresses a heterologous immunostimulatory polypetide.

According to a specific embodiment of the invention the influenza virus is influenza A virus.

In a further embodiment of the invention said truncated NS1 protein comprises at least 73 amino acids of the N-terminus of the respective wild type NS1 protein.

In a further embodiment of the invention said influenza virus has an IFN inducing phenotype.

Specifically, the influenza virus vector comprises a truncated NS1 protein that contains up to 122 amino acids, preferably up to 121 amino acids, preferably up to 120 amino acids, preferably up to 119 amino acids, preferably up to 118 amino acids, preferably up to 117 amino acids, preferably up to 116 amino acids, preferably up to 115 amino acids, preferably up to 114 amino acids, preferably up to 113 amino acids, preferably up to 112 amino acids, preferably up to 111 amino acids, preferably up to 110 amino acids, preferably up to 109 amino acids, preferably up to 108 amino acids, preferably up to 107 amino acids, preferably up to 106 amino acids, preferably up to 105 amino acids, preferably up to 104 amino acids, preferably up to 103 amino acids, preferably up to 102 amino acids, preferably up to 101 amino acids, preferably up to 100 amino acids, preferably up to 99 amino acids, preferably up to 98 amino acids, preferably up to 97 amino acids, preferably up to 96 amino acids, preferably up to 95 amino acids, preferably up to 94 amino acids, preferably up to 93 amino acids, preferably up to 92 amino acids, preferably up to 91 amino acids, preferably up to 90 amino acids, preferably up to 89 amino acids, preferably up to 88 amino acids, preferably up to 87 amino acids, preferably up to 86 amino acids, preferably up to 85 amino acids, preferably up to 84 amino acids, preferably up to 83 amino acids, preferably up to 82 amino acids, preferably up to 81 amino acids, preferably up to 80 amino acids, preferably up to 79 amino acids, preferably up to 78 amino acids, preferably up to 77 amino acids, preferably up to 76 amino acids, preferably up to 75 amino acids, preferably up to 74 amino acids, preferably up to 73 amino acids of the N-terminus of the NS1 protein.

According to a specific embodiment of the invention, the influenza virus comprises an NS1 protein which is between 100 and 117 amino acids, specifically between 100 and 110 amino acids length, more specifically it comprises 106 amino acids of the N-terminus of the NS1 protein and a heterologous immunostimulatory polypeptide. In a specific embodiment it is an influenza virus delNS106-GM-CSF, thus said influenza virus NS gene is encoding the N-terminal 106 amino acids of the NS1 protein and GM-CSF.

According to an embodiment of the invention, the IFN-sensitive tumor cells are selected from the group consisting of melanoma cells.

According to an embodiment of the invention the NS1 gene of the influenza virus vector is further modified by mutations in the noncoding region.

According to an embodiment of the invention the influenza virus vector comprises modifications of the genes encoding the NA and/or HA proteins.

According to a further embodiment of the invention the influenza virus comprises modifications of the polymerase genes encoding the PB1, PB2 and/or PA proteins.

According to a further embodiment of the invention the influenza virus comprises modifications of the genes encoding the M, and/or NP proteins.

According to a further embodiment of the invention the heterologous polypeptide is selected from the group consisting of tumor associated antigens, cytokines, IL2, IL15, GM-CSF, IL-15, MIP 1 alpha and MIP3 alpha.

The present invention also provides an immunogenic formulation comprising an influenza virus according to the invention, and a physiologically acceptable excipient.

According to the invention the influenza virus vector can be used in the preparation of a medicament for therapeutic treatment of a subject. Specifically, it can be used in the treatment of cancer.

The invention also provides a method for producing an influenza virus vector, wherein said virus is cultivated in the presence of tumor cells.

As an alternative a method is provided wherein the inventive influenza virus is produced, wherein said virus is expressing a cytokine and wherein said virus is obtained by passaging said influenza virus on tumor cells.

The invention also provides a combination of at least two influenza virus vectors according to the invention, wherein said viruses are of different types.

The embodiment of the invention also covers a combination of influenza virus of the invention for use in prime boost immunization, specifically for use in combination with immunomodulatory molecules.

The embodiment of the invention also covers a combination of influenza virus of the invention, wherein the immunomodulatory molecule is a protein, specifically an antibody, more specifically antagonists of CTLA-4, PD-1 or 4-1BB21.

FIGURES

Figures 1, 2:
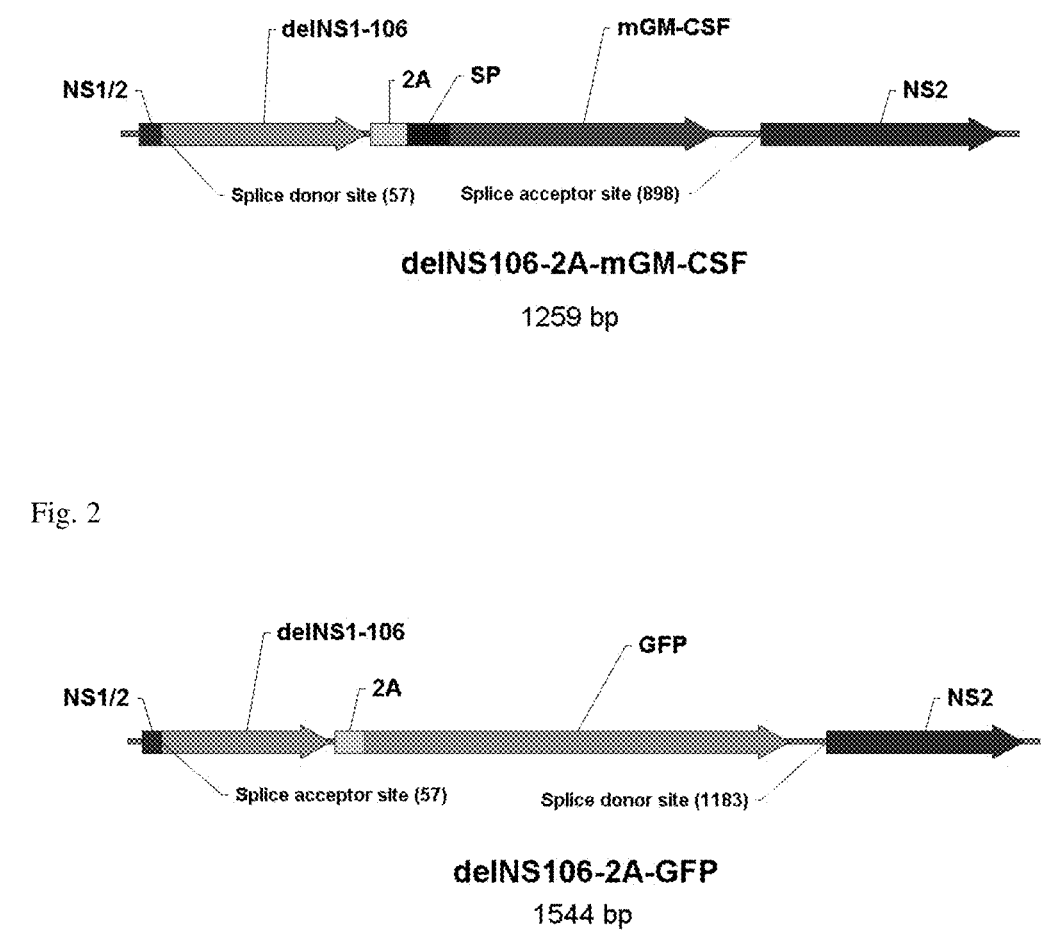

FIG. 1: The interferon antagonist NS1 was C-terminally truncated to 106 amino acids, thereby rendering the virus attenuated in interferon-competent cells. The open reading frame of murine GM-CSF was fused to the C-terminus of NS106 via a 2A peptide derived from the Foot-and-mouth disease virus. Upon translation of the NS106-2A-mGM-CSF fusion protein, the self-cleaving 2A peptide liberates mGM-CSF allowing it to be secreted through the ER-Golgi pathway.

FIG. 2: The interferon antagonist NS1 was C-terminally truncated to 106 amino acids, thereby rendering the virus attenuated in interferon-competent cells. The open reading frame of green florescent protein (GFP) was fused to the C-terminus of NS106 via a 2A peptide derived from the Foot-and-mouth disease virus. Upon translation of the NS106-2A-mGFP fusion protein the self-cleaving 2A peptide liberates GFP.

FIG. 3: Immunoblot: mGM-CSF in supernatants of Vero cells infected with the indicated viruses. Lane 1: delNS106-2A-GFP; lane 2: delNS106-2A-mGM-CSF; lane 3 and 4: 1 ng and 5 ng recombinant mGM-CSF expressed in E. coli.

Figure 4:
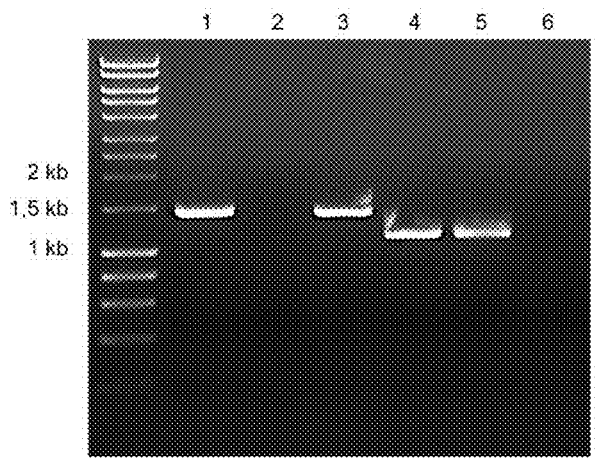

FIG. 4: RT-PCR analysis of passaged viruses demonstrating the genetic stability of the chimeric NS segments. Chimeric viruses obtained from transfection were serially passaged seven times in Vero cells. RT-PCR was carried out from viral RNA isolated from cell culture supernatants by using oligonucleotides homologous to the NS segment. PCR controls were included by using the respective chimeric delNS106 virus plasmid DNAs as templates. 1: delNS106-2A-GFP; 2: delNS106-2A-GFP RT-negative control; 3: pHW-delNS106-2A-GFP plasmid control; 4: pHW-delNS106-2A-mGM-CSF plasmid control; 5: delNS106-2A-mGM-CSF; 6: delNS106-2A-mGM-CSF RT-negative control.

Figure 5:
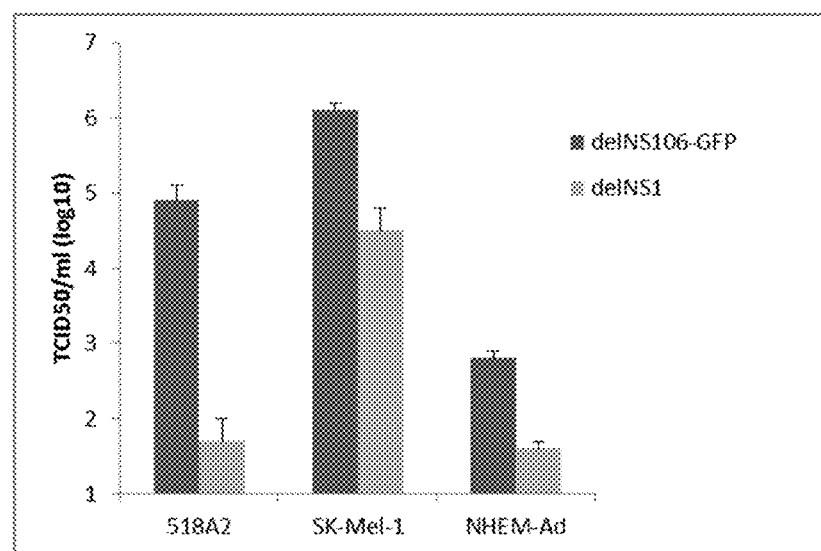

FIG. 5: Virus growth in human melanoma cells and normal human epidermal melanocytes. Cells were infected at an MOI of 0.1, and supernatants harvested 72h later were analysed for infectious titres by $TCID_{50}$ assay on Vero cells.

FIG. 6: Nucleotide sequence delNS106-2A-mGM-CSF (SEQ ID NO. 2).

FIG. 7: Amino acid sequence of NS106-2A-mGM-CSF (SEQ ID NO. 3). The truncated NS1 is indicated in bold letters, the 2A peptide in underlined letters and mGM-CSF in italic letters.

FIG. 8: Nucleotide sequence delNS106-2A-GFP (SEQ ID NO. 4).

FIG. 9: Amino acid sequence of NS106-2A-mGM-CSF (SEQ ID NO. 5). The truncated NS1 is indicated in bold letters, the 2A peptide in underlined letters and GFP in italic letters.

FIG. 10: Amino acid sequence of wild type influenza virus PR8 NS1 (SEQ ID NO. 1).

DETAILED DESCRIPTION OF THE INVENTION

An influenza virus coding for at least the first 73 amino acids of the NS1 gene which contains the RNA binding site, but not N-terminal amino acids from amino acid position 123 to 161 containing the so called effector domain, combines phenotypes highly desirable for a virus therapy candidate. While lacking the ability to block expression of IFN, these constructs retain the ability to replicate in interferon competent tumor cells. As a consequence, IFN is induced in the tumor tissue while viral replication allows expression of its genes and destruction of tumor cells. Surprisingly, while this mutant still grows in IFN competent tumor cells it shows at least 90-fold, specifically at least 100-fold, specifically at least 110-fold, specifically at least 120-fold, specifically at least 130-fold, specifically at least 140-fold, more specifically at least 150-fold decreased replication rate in normal cells such as melanocytes or any other non-tumor cells compared to the replication rate in the IFN competent tumor cells.

This inventive mutant virus has the optimal balance between sufficiently replicating in IFN sensitive and IFN competent tumor cells and being attenuated or even replication-deficient in normal cells. This is an important safety feature permitting its use in patients.

The term "sufficiently attenuated" according to the invention refers to a reduction of growth rate of at least 100-fold between IFN-sensitive tumor cells and normal cells such as, but not limited to primary melanocytes.

According to the embodiment of the invention, a method for determining replication-deficiency of an influenza virus can be as follows: the amount of infectious virus as determined in the supernatant about 72 hours (between 60 and 96 hours) after infection (output virus) of melanocytes must be lower as compared to the amount of infectious virus used in an inoculum for infection (input virus) of said cells. As an example, but not limiting to the scope of the invention, if an inoculum of 4.7 log TCID50 is used for virus infection and 3.4 log TCID50 after infection is obtained in the supernatant of the infected cells, it is a clear indication that the virus is replication deficient.

A recombinant influenza virus vector is thus provided comprising an isolated NS gene encoding a truncated NS1 protein of up to 122 amino acids, specifically of up to 117 amino acids, of the N-terminus of the respective wild type NS1 protein and a consecutive open reading frame encoding a heterologous immunostimulatory protein, wherein said vector (i) replicates in IFN-sensitive tumor cells and does not replicate or has highly reduced replication rate in normal cells, and (ii) expresses a heterologous immunostimulatory polypeptide.

Thus an influenza virus is provided that allows stable high expression of a heterologous protein.

The resulting viral vectors according to the present invention are specifically useful for a multiple purposes, such as oncolytic viral vectors expressing a transgene in a tumor microenvironment, antigenic vectors to induce an immunity against pathogenic molecules, and genetic stable vaccine backbone viruses.

The term "isolated" refers to a purified in vitro preparation, isolation and/or purification of a nucleic acid molecule such as a vector, plasmid or a virus according to the present invention, so that it is not associated with in vivo substances, or is substantially purified from in vitro substances. An isolated virus preparation is generally obtained by in vitro culture and propagation and is substantially free from other infectious agents.

A "recombinant" virus is one which has been manipulated in vitro, e.g., using recombinant DNA techniques, to introduce changes to the viral genome, or otherwise artificially generated.

According to the invention, the term "IFN-sensitivity" with regard to IFN-sensitive tumor cells is defined as at least 25% reduction of cell proliferation in the presence of IFNα-2a as compared to cell proliferation levels in the absence of IFNα-2a. For determining IFNα-2a-mediated reduction in cell growth of tumor cell lines a total of 2,500 cells are incubated with 5,000 I.U./ml IFNα-2a for 4 days. Cell proliferation is determined by the WST-1 proliferation assay (Muster et al., 2004).

As used in the invention, the term "polypeptide" refers to a polymer of amino acids and does not refer to a specific length of the product; thus, peptides, oligopeptides, and proteins are included within the definition of polypeptide. This term also does not refer to or exclude post expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

As used in this application, the term "amino acid" means one of the naturally occurring amino carboxylic acids of which proteins are comprised. The term "polypeptide" as described herein refers to a polymer of amino acid residues joined by peptide bonds, whether produced naturally or synthetically. Polypeptides of less than about 10 amino acids residues are commonly referred to as "peptides".

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A polypeptide or amino acid sequence "derived from" a designated nucleic acid sequence refers to a polypeptide having an amino acid sequence identical to that of a polypeptide encoded in the sequence, or a portion thereof wherein the portion consists of at least 15 amino acids, preferably at least 20 amino acids, more preferably at least 30 amino acids, and even more preferably at least 50 amino acids, or which is immunologically identifiable with a polypeptide encoded in the sequence. This terminology also includes a polypeptide expressed from a designated nucleic acid sequence. The maximum length of the respective heterologous polypeptide encoded by the NS gene sequence is 600 amino acids, specifically 500, specifically 400, specifically 300, specifically 200, specifically 150, specifically 100 amino acids.

In general, an immune response is generated to an antigen through the interaction of the antigen with the cells of the immune system Immune responses may be broadly categorized into two categories: humoral and cell mediated immune responses (e.g., traditionally characterized by antibody and cellular effector mechanisms of protection, respectively). These categories of response have been termed Th1-type response (cell-mediated response), and Th2-type immune response (humoral response).

Stimulation of an immune response can result from a direct or indirect response of a cell or component of the immune system to exposure to an immunogen Immune responses can be measured in many ways including activation, proliferation or differentiation of cells of the immune system (e.g., B cells, T cells, dendritic cells, APCs, macrophages, NK cells, NKT cells, etc.); up-regulated or down-regulated expression of markers and cytokines; stimulation of IgA, IgM, or IgG titer; splenomegaly (including increased spleen cellularity); hyperplasia and mixed cellular infiltrates in various organs. Other responses, cells, and components of the immune system that can be assessed with respect to immune stimulation are known in the art.

It is known that cytokine profiles can determine T cell regulatory and effector functions in immune responses. In some embodiments, Th1-type cytokines can be induced, and thus, the immunostimulatory polypeptide of the present invention can promote a Th1-type antigen-specific immune response including cytotoxic T-cells. However in other embodiments, Th2-type cytokines can be induced thereby promoting a Th2-type antigen-specific immune response.

The term "immunostimulating or immunostimulatory polypeptide" refers to any immunogenic polypeptide, which can be but is not limited to chemokines, specifically to cytokines, hematopoetic growth factors, tumor associated antigens, melanoma immunogens, etc.

The term "cytokine" or "chemokine" refers to bioactive molecules derived from cells and capable of affecting cells' behavior, e.g. growth, migration, killing capacity, differentiation, secretion, etc.

Chemokines, originally derived from chemoattractant cytokines, actually comprise more than 50 members and represent a family of small, inducible, and secreted proteins of low molecular weight (6-12 kDa in their monomeric form) that play a decisive role during immunosurveillance and inflammatory processes. Depending on their function in immunity and inflammation, they can be distinguished into two classes. Inflammatory chemokines are produced by many different tissue cells as well as by immigrating leukocytes in response to bacterial toxins and inflammatory cytokines like IL-1, TNF and interferons. Homing chemokines, on the other hand, are expressed constitutively in defined areas of the lymphoid tissues. They direct the traffic and homing of lymphocytes and dendritic cells within the immune system. These chemokines, as illustrated by BCA-1, SDF-1 or SLC, control the relocation and recirculation of lymphocytes in the context of maturation, differentiation, activation and ensure their correct homing within secondary lymphoid organs.

According to the present invention it has been shown that biologically active cytokines or chemokines or derivatives or fragments thereof can be stably and efficiently expressed by the present influenza virus vector.

According to the invention the proteins can be selected from but are not limited to the group consisting of IL2, IL15, GM-CSF, MIP 1alpha, MIP3 alpha or functional fragments or derivatives thereof.

The nucleotide sequence encoding the heterologous polypeptide may be directly fused to the 3'end of the gene encoding the truncated NS1 protein via short linker sequences up to 20 amino acids length. Said linker sequences can be, but are not limited to viral 2A sequences Said 2A peptides may be from Picorna viridae virus family, such as foot-and-mouth disease virus (FMDV) and equine rhinitis A virus (ERAV), and other viruses such as the porcine teschovirus-1 and the insect virus *Thosea asigna* virus (TaV)3. The 2A sequences are relatively short peptides, of about 20 amino acids long, depending on the virus of origin, and can comprise the consensus motif Asn-Pro-Gly-Pro.

Specifically the influenza virus is derived from influenza A virus, influenza B virus or influenza C virus.

The NS1 protein of influenza virus is a multifunctional protein that consists of 230 to 280 amino acids and is early and abundantly synthesized in infection. It counters cellular antiviral activities and is a virulence factor. By the activity of its carboxy terminal region, the NS1 protein is able to inhibit the host mRNA's processing mechanisms.

Further, it facilitates the preferential translation of viral mRNA by direct interaction with the cellular translation initiation factor. By binding to dsRNA and interaction with putative cellular kinase(s), the NS1 protein is able to prevent the activation of interferon (IFN) inducible dsRNA-activated kinase (PKR), 2'5'-oligoadenylate synthetase system and cytokine transcription factors.

The N terminal part of NS1 binds to RIG-I and inhibits downstream activation of IRF-3, preventing the transcriptional induction of IFN-β. Therefore the NS1 protein inhibits the expression of IFN-α or IFN-β genes, delays the development of apoptosis in the infected cells, and prevents the formation of the antiviral state in neighboring cells.

The NS1 protein of the influenza virus vector according to the invention comprises a functional RNA binding domain. The primary function of this domain located at the amino end of the NS1 protein (amino acids 1-73) is binding dsRNA and inhibiting the 2'5'oligo (A) synthetase/RNase L pathway (Min J. et al., Proc. Natl. Acad. Sci, 2006, 103: 7100-7105; Chien et al., Biochemistry, 2004, 43(7): 1950-62) as well as the activation of a cytoplasmic RNA helicase, RIG-I, retinoic acid-inducible protein I (Yoneyama M. et al., Nat. Immunol., 2004, 5: 730-737).

The influenza virus A/Puerto Rico/8/34 (PR8) NS gene segment can be found in GenBank (e.g., GenBank No. AF389122.1 GI21693177). The open reading frame for the PR8 NS1 is from nucleotides 27 to 719. In specific embodiments, the NS1 ORF is further codon optimized (without changing the protein sequence) to, e.g., avoid repetitive sequences, to increase protein expression and/or to increase the stability of the NS gene segment. Techniques for codon optimization are known in the art.

Specifically, the influenza virus vector comprises a truncated NS1 protein that contains up to 122 amino acids, preferably up to 121 amino acids, 120 amino acids, preferably up to 119 amino acids, preferably up to 118 amino acids, preferably up to 117 amino acids, preferably up to 116 amino acids, preferably up to 115 amino acids, preferably up to 114 amino acids, preferably up to 113 amino acids, preferably up to 112 amino acids, preferably up to 111 amino acids, preferably up to 110 amino acids, preferably up to 109 amino acids, preferably up to 108 amino acids, preferably up to 107 amino acids, preferably up to 106 amino acids, preferably up to 105 amino acids, preferably up to 104 amino acids, preferably up to 103 amino acids, preferably up to 102 amino acids, preferably up to 101 amino acids, preferably up to 100 amino acids, preferably up to 99 amino acids, preferably up to 98 amino acids, preferably up to 97 amino acids, preferably up to 96 amino acids, preferably up to 95 amino acids, preferably up to 94 amino acids, preferably up to 93 amino acids, preferably up to 92 amino acids, preferably up to 91 amino acids, preferably up to 90 amino acids, preferably up to 89 amino acids, preferably up to 88 amino acids, preferably up to 87 amino acids, preferably up to 86 amino acids, preferably up to 85 amino acids, preferably up to 84 amino acids, preferably up to 83 amino acids, preferably up to 82 amino acids, preferably up to 81 amino acids, preferably up to 80 amino acids, preferably up to 79 amino acids, preferably up to 78 amino acids, preferably up to 77 amino acids, preferably up to 76 amino acids, preferably up to 75 amino acids, preferably up to 74 amino acids, preferably up to 73 amino acids of the N-terminus.

According to a preferred embodiment, the influenza virus is a delNS106 virus, thus containing 106 amino acids of the N-terminus of the NS1 protein and further expressing a heterologous polypeptide, specifically a cytokine or functional derivative thereof. According to a further embodiment the inventive influenza virus vector comprises an NS gene encoding truncated NS1 protein of 106 amino acids and a heterologous immunostimulatory polypeptide, wherein said polypeptide may be within the same reading frame.

The invention also provides a plasmid or any other expression construct containing a first nucleotide sequence encoding a truncated NS1 protein of 73 to 122 amino acids, specifically of 95 to 117 amino acids, specifically of 100 to 110 amino acids, specifically of 106 amino acids of the N-terminus of the full-length NS1 protein and a second nucleotide sequence encoding a heterologous immunostimulatory polypeptide. In a further embodiment, said nucleotide sequences may constitute one single open reading frame encoding the truncated NS1 protein and the heterologous immunostimulatory protein, optionally separated by a linker sequence of up to 100 nucleotides.

According to a further embodiment of the invention, essential parts of the effector domain such as the PKR interaction sites (Mok et al., J Virol., 86: 12605) of the NS1 protein of influenza virus vector are deleted. The effector domain interacts with cellular proteins to inhibit mRNA nuclear export. The effector domain is located at the C-terminal part of the NS1 protein. According to Schultz et al., the effector domain is specifically located between amino acid residues 117 and 161, other literature locates the effector domain between 134 and 161.

According to an embodiment of the invention, the influenza gene segments can be derived from the same or from different influenza strains, either pandemic or interpandemic ones. This can result in reassorted influenza viruses which combine the genes for the surface glycoproteins hemagglutinin (HA) and/or neuraminidase (NA) of actual interpandemic viruses with five or six or seven RNA segments coding for other proteins from the attenuated master strain, i.e. 6/2 combination or 7/1 reassortants or 5/3 reassortants containing HA, NA and M segments of a circulating strain respectively.

Examples of influenza A viruses include subtype H10N4, H10N5, H10N7, H10N8, H10N9, H11N1, H11N13, H11N2, H11N4, H11N6, H11N8, H11N9, H12N1, H12N4, H12N5, H12N8, H13N2, H13N3, H13N6, H13N7, H14N5, H14N6, H15N8, H15N9, H16N3, H1N1, H1N2, H1N3, H1N6, H1N9, H2N1, H2N2, H2N3, H2N5, H2N7, H2N8, H2N9, H3N1, H3N2, H3N3, H3N4, H3N5, H3N6, H3N8, H3N9, H4N1, H4N2, H4N3, H4N4, H4N5, H4N6, H4N8, H4N9, H5N1, H5N2, H5N3, H5N4, H5N6, H5N7, H5N8, H5N9, H6N1, H6N2, H6N3, H6N4, H6N5, H6N6, H6N7, H6N8, H6N9, H7N1, H7N2, H7N3, H7N4, H7N5, H7N7, H7N8, H7N9, H8N4, H8N5, H9N1, H9N2, H9N3, H9N5, H9N6, H9N7, H9N8, and H9N9. Specifically preferred are H1N1, H1N2, H3N2 and H5N1.

The HA glycoprotein can be of any subtype, specifically it is of subtype H1 and H3.

The term "IFN-inducing phenotype" according to the invention means that significant amounts of IFN can be detected in supernatants of infected cells with the viral vector.

Tumor cells can be any cells involved in tumor growth and metastasis, specifically derived or originated from solid tumors. Specifically said cells can be selected from the group of melanoma cells, such as but not limited to SK-Mel 28 and SK-Mel 1 cells, 518A2, colon carcinoma cells like for example COCA 2 cells, glioma cells, lung cancer cells or breast cancer cells.

"IFN sensitive tumor cells" such as, but not limited to, 518A2 are reduced in cell growth in the presence of IFNalpha-2a to more than 50%. "Interferon resistant tumor cells" such as, but not limited to, SK-Mel1 are inhibited in its growth to less than 50%. For determining cell growth, cells are incubated in the presence of 5,000 I.U./ml IFNalpha-2a for 4 days and cell proliferation is determined. Cell proliferation in the absence of IFN-alpha-2a is considered 100%.

Specifically, modifications in non-coding regions of the NS1 gene can be but are not limited to the first 8 nucleotides at the 5' and 3'ends, however not limited to conserved regions.

The influenza virus vector can further contain modifications of the genes encoding the NA and/or HA, M or NP proteins, modifications of the polymerase genes encoding the PB1, PB2 and/or PA proteins. Specifically, said modifications result in deletion or replacement or insertion of amino acids within said proteins which may result in modifications of functionality, antigenicity, secondary structure of the so modified proteins.

The influenza virus vector of the invention can be formulated as pharmaceutical preparation optionally containing pharmaceutically acceptable additives, carriers and/or stabilizers.

The term "pharmaceutically acceptable" means approved by a regulatory agency of the Federal or a state government or listed in the U.S.

The term "carrier" refers to a diluent, adjuvant, excipient, or vehicle with which the pharmaceutical composition (e.g., immunogenic or vaccine formulation) is administered. Saline solutions and aqueous dextrose and glycerol solutions can also be employed as liquid carriers, particularly for injectable solutions. Suitable excipients include starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should be selected according to the mode of administration. The particular formulation may also depend on whether the virus is live or inactivated.

The term adjuvant refers to a compound or mixture that enhances the immune response to an antigen. The term "stabilizers" refers to any agent that can increase the stability of the inventive virus, for example it can be bovine serum albumin, sugars, chitosan, dextrans, PEGs etc.

Methods of administration include but are not limited to intratumoral, intradermal, intramuscular, intraperitoneal, intravenous, intranasal, epidural or oral routes.

In a preferred embodiment it may be desirable to introduce the medicament into the lungs by any suitable route. Pulmonary administration can also be employed, using e.g. an inhaler or nebulizer or formulate it with an aerosolizing agent.

The pharmaceutical preparation can also be delivered by a controlled release system, like a pump.

Alternatively, a ready-to-use infusion solution is provided. Alternatively, the preparation can be formulated as powder which is solved in appropriate aqueous solutions immediately before application.

The influenza virus vector of the invention can be used in the preparation of a medicament for therapeutic treatment of a subject, specifically it can be used for virotherapy, specifically for tumor treatment or oncolytic treatment of cancer.

The amount of the pharmaceutical composition of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for administration are generally about $10^4$ $^-5\times10^8$ pfu and can be administered once, or multiple times with intervals as often as needed. Pharmaceutical compositions of the present invention comprising $10^4$ $^-5\times10^8$ pfu of inventive viruses can be administered intratumorally, intranasally, intratracheally, intramuscularly or subcutaneously. Effective doses may be extrapolated from dose-response curves derived from in vitro or animal model test systems.

The term "oncolytic treatment of cancer", means treating cancer cells with an agent such as a virus that specifically kills cancer cells, but does not harm normal cells.

The combination of at least two influenza virus vectors according to the invention wherein said viruses are of different types is also covered. Also a combination of three or more is covered by the embodiment of the invention.

A specific combination of virus vectors may be a combination of influenza virus A and B or influenza virus A and C or influenza virus B and C.

The term "prime boost immunization" means that multiple, i.e. at least two, at least three, at least four, at least five immunizations are given. Prime-boost immunization can be performed by administration of the same influenza virus vectors or combinations thereof (homologous prime boost), however, as an alternative, different influenza virus vectors or combinations thereof can be administered as heterologous prime boost. Said influenza virus vector can further be combined with immunomodulatory molecules, preferably are selected, but not limited to enzymes, members of the immunoglobulin superfamily, such as antibodies and antibody domains or fragments such as such as Fab, Fv or scFv, cytokines, vaccine antigens, growth factors and peptides or immunomodulatory antagonists like CTLA-4, PD-1 or 4-1BB21.

For developing reassortants and/or expression of modified influenza virus strains a reverse genetics system on Vero cells can be used. The technology is already well known in the art (Pleschka S. et al., 1996, J. Virol., 70(6), 4188-4192; Neumann and Kawaoka, 1999, Adv. Virus Res., 53, 265-300; Hoffmann et al., 2000, Proc Natl Acad Sci USA., 97: 6108-13). Alternatively, the technology based on RNPs as described by Enami and Enami (J Virol, 2000, 74, 12, pp. 5556-5561) can be used for developing reassortants.

The method for producing an influenza virus is also covered by the embodiment of the invention, wherein said virus is expressing a cytokine and wherein said virus is obtained by passaging said influenza virus on tumor cells.

More specifically, said method can be described by the steps of passaging influenza virus in tumor cells, selecting influenza virus vector with increased propagation rate and isolating and sequencing the respective high-growing influenza virus.

The invention furthermore comprises the following items:

1. A recombinant influenza virus vector comprising an NS gene encoding a truncated NS1 protein of at least 73 amino acids and up to 122 amino acids, specifically up to 117 amino acids of the N-terminus of the respective wild type NS1 protein, wherein said vector (i) replicates in IFN-sensitive tumor cells and is attenuated and replication-deficient in normal, non-tumor cells, and (ii) expresses a heterologous immunostimulatory polypeptide.

2. The influenza virus of item 1, wherein said virus is influenza A virus.

3. The influenza virus of item 1 or 2, wherein said truncated NS1 protein comprises at least 73 amino acids of the N-terminus of the respective wild type NS1 protein.

4. The influenza virus according to any one of items 1 to 3, wherein said influenza virus has an IFN inducing phenotype 5. The influenza virus vector according to any one of items 1 to 4, wherein said truncated NS1 protein contains up to 120 amino acids, preferably up to 115 amino acids, preferably up to 110 amino acids, preferably up to 105 amino acids, preferably up to 100 amino acids, preferably up to 95 amino acids, preferably up to 90 amino acids, preferably up to 85 amino acids, preferably up to 80 amino acids, preferably up to 75 amino acids of the N-terminus.

6. The influenza virus vector according to any one of items 1 to 5, wherein the IFN-sensitive tumor cells are selected from the group consisting of melanoma cells.

7. The influenza virus vector according to any one of items 1 to 6, wherein the NS1 gene is further modified by mutations in the noncoding region.

8. The influenza virus vector according to any one of items 1 to 7 comprising modifications of the genes encoding the NA and/or HA proteins.

9. The influenza virus vector according to any one of items 1 to 8 comprising modifications of the polymerase genes encoding the PB1, PB2 and/or PA proteins.

10. The influenza virus vector according to any one of items 1 to 9 comprising modifications of the genes encoding the M, and/or NP proteins.

11. The influenza virus vector according to any one of items 1 to 10, wherein the heterologous polypeptide is selected from the group consisting of tumor associated antigens, cytokines, IL2, IL15, GM-CSF, MIP 1 alpha, MIP3 alpha.

12. Pharmaceutical formulation comprising an influenza virus vector according to any one of items 1 to 10.

13. An immunogenic formulation comprising an influenza virus according to any one of items 1 to 11, and a physiologically acceptable excipient.

14. The influenza virus vector according to any one of items 1 to 11 for use in the preparation of a medicament for therapeutic treatment of a subject.

15. The influenza virus vector according to any one of items 1 to 11 for use in virotherapy, tumor treatment, oncolytic treatment against cancer.

16. Method for producing an influenza virus vector according to any one of items 1 to 11, wherein said virus is cultivated in the presence of tumor cells.

17. Combination of at least two influenza virus vectors according to any one of items 1 to 11, wherein said viruses are of different types.

18. Combination of an influenza virus vector according to items 15 or 16 with immunomodulatory molecules.

19. Combination according to item 18, wherein the immunomodulatory molecule is a protein.

20. Combination according to item 19, wherein the protein is an antibody.

21. Combination according to any one of items 18 to 20, wherein the immunomodulatory molecules are antagonists of CTLA-4, PD-1 or 4-1BB21.

22. Combination according to any one of items 17 to 21 for use in prime boost immunization.

23. Method for producing an influenza virus according to any one of items 1 to 11, wherein said virus is expressing a cytokine and wherein said virus is obtained by passaging said influenza virus on tumor cells.

The examples described herein are illustrative of the present invention and are not intended to be limitations thereon. Different embodiments of the present invention have been described according to the present invention. Many modifications and variations may be made to the techniques described and illustrated herein without departing from the spirit and scope of the invention. Accordingly, it should be understood that the examples are illustrative only and are not limiting upon the scope of the invention.

EXAMPLES

Example 1

Cells and Viruses

Human melanoma cell lines SK-MEL 28 (ATCC, Manassas, Va.) and 518 A2 are grown in DMEM (Gibco BRL, Rockville, Md.) supplemented with 10% FCS (Gibco BRL). The human melanoma cell line SK-MEL 1 (ATCC) is cultured in minimum essential medium (MEM, Eagle) (Gibco BRL) containing 10% FCS, 0.1 mM non-essential amino acids, 1.0 mM sodium pyruvate and Earle's BBS. The primary melanocytic cell line NHEM (Szabo Scandic, Vienna, Austria) is grown in melanocyte growth medium (Clonetics Cambrex, East Rutherford, N.J.). Vero cells adapted to grow on serum-free medium (ATCC) are maintained in serum-free AIMV medium (Gibco BRL). Wildtype influenza virus contains a transfected NS wt gene segment and encodes a wild-type NS1 protein of 230 amino acids. NS1-106 contains an NS gene segment with the first 106 C-terminal amino acids. The delNS1 virus contains a complete deletion in the NS gene segment. For propagation of the viruses, Vero cells are infected at a multiplicity of infection (m.o.i.) of 0.1 and incubated in AIMV medium (Gibco BRL) containing 5 ug/ml trypsin (Sigma) at 37° C. for 3 days. Virus concentrations are determined by plaque assays on Vero cells.

Viral Replication

Cells are washed with PBS and infected with the wildtype virus and the corresponding NS1 deletion mutants at an m.o.i. of 0.1. After incubation for 30 min, the inoculum is removed, cells are washed with PBS, overlaid with serum-free AIMV medium containing 2.5 ug/ml trypsin (Sigma) and incubated at 37° C. for 48 hr. Supernatants are assayed for infectious virus particles on Vero cells. To evaluate the effect of IFN on viral growth, $10^6$ cells are incubated in the absence or presence of 5,000 I.U./ml IFN-2alfa at 37° C. for 16 hr. Virus infection is done thereafter. Virus titers are determined in the supernatants 48 hr post-infection.

Replication of NS1-deletion Mutants in IFN-competent, IFN-deficient Tumor Cells, and Normal (Non-malignant) Cells IFN-sensitive and IFN-resistant tumor cell lines, as well as normal cells such as melanocytes are infected with different NS1 deletion mutants and the progeny virus titer in the supernatant of cell lines infected is determined. The growth properties of the different NS1 deletion mutants are compared. Viral growth correlates well with the IFN-sensitivity. In the most IFN-sensitive (IFN-competent) tumor cell lines 518-A2 and SK-MEL28 the delNS1 virus does not grow at all. In contrast the wild type and the deletion mutant NS1-106 grow efficiently on these cells. In SK-MEL1 which is considered to be an IFN-resistant cell line, also the delNS1 mutant grew although to a lesser extent than the wild-type and the other NS deletion mutants. These results suggest that delNS1 replication is dependent on IFN-resistance while replication of and NS1-106 is not.

One requirement of a conditionally replicating virus for usage as a therapeutic agent is its restricted growth in nonmalignant cells. Importantly, in cultured primary melanocytes NHEM and primary keratinocytes which are cells present in normal human skin only the wild-type replicates efficiently but not the NS deletion mutant NS1-106 and delNS1. In neither of these cells, infection with these mutants results in release of infectious particles into the supernatant. In contrast, these cell lines support viral replication of the wild-type virus.

Prime/Boost with Antigenically Different Candidates

In the B16 mouse melanoma model (Overwijk WW, Restifo NP 2001), mice are treated 3 times with an A type vector followed by treatment 3 times with a B type vector. The anti-tunmoral activity of the combination of vectors belonging to different influenza virus types is significantly better as compared to treatment with either vector alone.

Example 2

The generation and characterisation of a mouse GM-CSF (Granulocyte-Macrophage Colony Stimulating Factor)-expressing Influenza A H1N1 NS1 deletion virus is described.

The interferon antagonist NS1 was C-terminally truncated to 106 amino acids, thereby rendering the virus attenuated in interferon-competent cells.

The open reading frame of murine GM-CSF was fused to the C-terminus of NS106 via a 2A peptide derived from the Foot-and-mouth disease virus (FIG. 1). Upon translation of the NS106-2A-mGM-CSF fusion protein the self-cleaving 2A peptide liberates mGM-CSF allowing it to be secreted through the ER-Golgi pathway. Alternatively, the ORF of green fluorescent protein (GFP) was inserted into the delNS106 segment (FIG. 2).

The delNS106-2A-mGM-CSF virus and the delNS106-2A-GFP virus were generated by eight plasmid transfection of Vero cells.

The chimeric delNS106 segments proved to be genetically stable over seven consecutive virus passages in Vero cells as assessed by RT-PCR and sequencing.

Significant secretion of mGM-CSF into the supernatant of infected delNS106-2A-mGM-CSF virus Vero cells was demonstrated by ELISA (111+/−14 ng/ml) and immunoblotting. Similarly, a strong GFP expression was observed Vero cells infected with delNS106-2A-GFP virus.

Both viruses grew to high titres in Vero cells (7.9+/−0.3 log 10/ml for delNS106-2A-mGM-CSF and 8.6+/−0.2 log 10/ml for delNS106-2A-GFP) as assessed by tissue culture infectious dose 50 (TCID50) assay.

In conclusion, genetically stable Influenza A H1N1 NS1 deletion viruses were generated that express significant amounts of murine GM-CSF and GFP and grow to high titres in Vero cells.

Cell Culture

Vero cells were grown under serum-free conditions in OptiPro SFM (Life Technologies) supplemented with 2 mM GlutaMax I (Life Technologies) at 37° C. and 5% CO2. For virus propagation 5 µg/ml porcine trypsin (Sigma Aldrich) and 250 ng/ml Amphotericin B (Sigma Aldrich) were added to the medium (Roethl et al., 2011, Antimycotic-antibiotic amphotericin B promotes influenza virus replication in cell culture. *J Virol* 85, 11139-11145).

Virus Generation and Propagation

The delNS106-2A-mGM-CSF and the delNS106-2A-GFP virus were rescued by eight-plasmid transfection of Vero cells as previously described (Hoffmann et al., 2000, A DNA transfection system for generation of influenza A virus from eight plasmids. *Proceedings of the National Academy of Sciences of the United States of America* 97, 6108-6113; Romanova et al., 2009, Preclinical evaluation of a replication-deficient intranasal DeltaNS1 H5N1 influenza vaccine. *PloS one* 4, e5984; Wacheck et al., 2010, A novel type of influenza vaccine: safety and immunogenicity of replication-deficient influenza virus created by deletion of the interferon antagonist NS1. *The Journal of infectious diseases* 201, 354-362). The viral segments are derived from the IVR-116 vaccine strain (WHO). They originate from A/Puerto Rico/8/34 (PA, PB2, NP, M, and NS), A/Texas/1/77 (PB1), and A/New Caledonia/20/99 H1N1 (HA, NA). The chimeric segments delNS106-2A-mGM-CSF and delNS106-2A-GFP were obtained by gene synthesis (Geneart) and cloned into pHW2000. Briefly, Vero cells were trypsinised and resuspended in Nucleofector solution. Following addition of eight pHW2000 derivatives (Hoffmann et al., 2000) coding for the respective viral segments electroporation was performed with a Nucleofector II device (Lonza) according to the manufacturer's instruction. Transfected cells were seeded in 6-well plates and incubated at 37° C. and 5% CO2. Once a complete cytopathic effect was observed, viruses were frozen at −80° C. until further usage. Virus passaging in Vero cells was performed in 6-well plates.

Analysis of GM-CSF Expression

Vero cells were infected in OptiPro medium for 3 hours at 37° C. at a multiplicity of infection of approximately 5. Subsequently, fetal calf serum was added to a final concentration of 2.5% v/v to prevent degradation of GM-CSF.

Analysis of GM-CSF as performed by ELISA (Ebioscience) according to the manufacturer's instructions and immunoblotting using a polyclonal rabbit anti mouse-GM-CSF antibody (Abcam) and a secondary anti-rabbit IgG alkaline phosphatase conjugate.

RT-PCR Analysis of Viral RNA

Viral RNA was isolated from supernatants of infected Vero cells using a QIAmp Viral RNA mini kit (Qiagen). RNA was reverse transcribed using Superscript III reverse transcriptase and Uni12 oligonucleotide (5'-AGCAAAAGCAGG-3', SEQ ID NO. 6). As negative controls, RNA samples were processed without the addition of reverse transcriptase. PCR amplification was performed with Phusion HF polymerase (Thermo Scientific) using the oligonucleotides NSRTLen (5'-AGCAAAAGCAGGGT-GACAAAG-3', SEQ ID NO. 7) and NS834 (5'-CTCTT-GCTCCACTTCAAGC-3', SEQ ID NO. 8). PCR products were separated by agarose gel electrophoresis, gel extracted using a GeneJet kit (Thermo Scientific) and custom sequenced at VBC Biotech (Vienna, Austria). The following primers were used for sequencing: NSRTLen, NS834, NSGFP383s: 5'-CTTAAACTTGCAGGAGATGTG-3', SEQ ID NO. 9 and NSGFP1208as: 5'-GATGAGGACTC-CAACTGC-3', SEQ ID NO. 10.

Virus Titration

Infectious virus titers in 50% tissue culture infectious doses (TCID50)/ml were determined in Vero cells seeded at a density of 1.5×10E4/well the day before infection. Tenfold virus dilutions were prepared. After three days, the wells were examined microscopically and scored as infected or non-infected by determining the presence or absence of a cytopathic effect. The virus titer was calculated according to the method of Reed and Muench (Reed & Muench, 1938).

Results and Discussion

Vero cells were transfected by electroporation of eight pHW2000 derivatives containing each one of the viral segments. Already four days after transfection a complete cytopathic effect was observed for both, delNS106-2A-mGM-CSF and the delNS106-2A-GFP indicating a high growth potential of the viruses.

To assess mGM-CSF expression, Vero cells were infected with either delNS106-2A-mGM-CSF or delNS106-2A-GFP virus at an MOI of approximately five and incubated for 24h. Supernatants were analysed by ELISA. While for cells infected with delNS106-2A-mGM-CSF virus a concentration of 111+/−14 ng/ml mGM-CSF was measured, no mGM-CSF expression was detected in cells infected with delNS106-2A-GFP virus.

In order to verify correct processing of mGM-CSF, supernatants were analysed by immunoblotting using an antibody specific for mGM-CSF.

FIG. 3 shows an immunoblot: mGM-CSF in supernatants of Vero cells infected with the indicated viruses. Lane 1: delNS106-2A-GFP; lane 2: delNS106-2A-mGM-CSF; lane 3 and 4: 1 ng and 5 ng recombinant mGM-CSF expressed in *E. coli*.

Due to glycosylation, mGM-CSF migrated as several bands in the range of approximately 15 to 25 kDa. In contrast, *E. coli*-derived mGM-CSF that lacks glycans migrated as a single band at approximately 14 kDa.

Analogously, a strong expression of GFP was detected in Vero cells infected with delNS106-2A-GFP virus In order to evaluate the genetic stability of the chimeric NS segments, both viruses were propagated through seven consecutive passages in Vero cells. Viral RNA was isolated and subjected to RT-PCR using oligonucleotides specific for the NS segment. As shown in 4, NS RT-PCR products for both viruses migrated at the same height as their corresponding plasmid controls indicating the genetic stability of the chimeric NS segments. RT negative controls were negative for both viruses ruling out the possibility that PCR products were amplified from residual plasmid DNA derived from transfection. Sequencing confirmed the lack of mutations in the chimeric delNS segment for both viruses (data not shown).

FIG. 4 shows the RT-PCR analysis of passaged viruses demonstrating the genetic stability of the chimeric NS segments. Chimeric viruses obtained from transfection were serially passaged seven times in Vero cells. RT-PCR was carried out from viral RNA isolated from cell culture supernatants by using oligonucleotides homologous to the NS segment. PCR controls were included by using the respective chimeric delNS106 virus plasmid DNAs as templates. 1: delNS106-2A-GFP; 2: delNS106-2A-GFP RT-negative control; 3: pHW-delNS106-2A-GFP plasmid control; 4: pHW-delNS106-2A-mGM-CSF plasmid control; 5: delNS106-2A-mGM-CSF; 6: delNS106-2A-mGM-CSF RT-negative control.

Importantly, both viruses are capable of growing to high titres. Supernatants obtained from passage 7 were analysed by TCID50 assay. For delNS106-2A-mGM-CSF 7.9+/−0.3 log 10 TCID50/ml and for delNS106-2A-GFP 8.6+/−0.2 log 10 TCID50/ml were detected.

Example 3

Cells

Human melanoma cell lines SK-MEL 1 (ATCC, Manassas, Va.) and 518 A2 were grown in DMEM/F12 medium (Invitrogen) supplemented with 10% FCS (Invitrogen) and 2 mM GlutaMax I supplement (Invitrogen) at 37° C. and 5% CO2.

Adult normal human epidermal melanocytes (NHEM-Ad; Clonetics) were grown according to the manufacturer's instructions in supplemented MBM-4 basal medium (Clonetics) instructions at 37° C. and 5% CO2.

Vero cells adapted to grow on serum-free medium (ATCC) were maintained in serum-free OptiPro medium supplemented with 2 mM GlutaMax I supplement.

Virus Generation

For virus generation seven pHW2000 derivatives (Hoffmann et al. 2000, Proc Natl Acad Sci USA. 97:6108-13) containing the segments PA, PB2, M and NP from Puerto Rico/8/34, PB1 from A/Texas/1/77, and HA, NA from A/New Caledonia/20/99 H1N1, as well as a protein expression plasmid coding for Influenza A PR8 NS1 (pCAGGS-NS1(SAM); (Salvatore et al. 2002, J Virol. 76:1206-12)) were used together with a pHW2000 derivative containing either the delNS106-GFP segment or the delNS1 segment for cotransfection of Vero cells. Following transfection, to support virus replication Vero cells were cultured in serum-free medium (OptiPro; Invitrogen) in the presence of 5 µg/ml trypsin. Four days after transfection 100% CPE was observed and rescued viruses were frozen or further amplified in Vero cells.

Virus Replication in Human Melanoma Cells and Normal Human Melanocytes

Adherent 518A2 cells were seeded the day before infection in 6-well plates. Before infection cells were washed twice with PBS and overlaid with serum-free OptiPro medium containing 2 mM GlutaMax I supplement and 5 µg/ml trypsin.

SK-Mel-1 suspension cells were washed twice with PBS, resuspended in OptiPro medium containing 2 mM GlutaMax I supplement and 5 µg/ml trypsin and seeded in 6-well plates.

NHEM-Ad were seeded four days before infection in supplemented MBM-4 basal medium, washed twice with PBS and overlaid with OptiPro medium containing 2 mM GlutaMax I supplement and 0.5 µg/ml trypsin.

Cells were infected at a multiplicity of infection (MOI) of 0.1 with either delNS106-GFP or delNS1 virus and incubated for 72 hours at 37° C. Supernatants are assayed for infectious virus particles in Vero cells by TCID50 assay.

In the most IFN-sensitive (IFN-competent) tumor cell line 518-A2, the delNS106-GFP virus grew to more than 4.9 log TCID50/ml while the delNS1 virus reached a titre of only 1.7 log TICD50/ml (Figure xx). In the interferon-resistant cell line SK-Mel-1, the delNS106-GFP virus grew to 6.1 log TCID50/ml while delNS1 yielded a titre of 4.5 log TCID50/ml.

In normal human epidermal melanocytes delNS106-GFP grew to a titre of 2.8 log TCID50/ml, which surprisingly is more than two log TCID50/ml lower than in the interferon-sensitive 518-A2 cells. This result indicates that this virus has an optimal conditional replication phenotype. Since in melanocytes the titre of the inoculum is higher than the titre in the supernatant after infection, this virus is considered replication-deficient. DelNS1 virus reached 1.6 log TCID50/ml a similar level as in the interferon-sensitive 518-A2 cells (1.7 log TCID50/ml), and is therefore not considered to have an optimal conditional replication phenotype.

FIG. 5: Virus growth in human melanoma cells and normal human epidermal melanocytes. Cells were infected at an MOI of 0.1, and supernatants harvested 72h later were analysed for infectious titres by $TCID_{50}$ assay on Vero cells.

The invention claimed is:

1. A recombinant influenza B virus vector comprising an NS gene encoding a truncated NS1 protein consisting of 106 amino acids of the N-terminus of the respective wild type NS1 protein, wherein the vector:
   (i) replicates in IFN-sensitive tumor cells and in IFN-resistant tumor cells, and is attenuated in normal cells, and
   (ii) expresses a heterologous immunostimulatory polypeptide, wherein the heterologous polypeptide is a tumor associated antigen.

2. The influenza virus vector of claim 1, wherein the influenza virus vector has an IFN-inducing phenotype.

3. The influenza virus vector of claim 1, wherein the IFN-sensitive tumor cells are melanoma cells.

4. The influenza virus vector of claim 1, wherein the NS gene is further modified by mutations in the noncoding region.

5. The influenza virus vector of claim 1, wherein the vector comprises modifications of the genes encoding the NA and/or HA proteins.

6. The influenza virus vector of claim 1, wherein the vector comprises modifications of the polymerase genes encoding the PB1, PB2, and/or PA proteins.

7. The influenza virus vector of claim 1, wherein the vector comprises modifications of the genes encoding the M and/or NP proteins.

8. A composition comprising the influenza virus vector of claim 1 and a physiologically acceptable excipient.

9. The composition of claim 8, comprising at least two influenza virus vectors, wherein each vector is a vector according to claim 1, and wherein said vectors are derived from at least two types of influenza viruses selected from the group consisting of type A influenza viruses, type B influenza viruses, and type C influenza viruses.

10. The composition of claim 8, further comprising an immunomodulatory molecule.

11. The composition of claim 10, wherein the immunomodulatory molecule is an antibody.

12. The composition of claim 10, wherein the immunomodulatory molecule is an antagonist of CTLA-4, PD-1 or 4-1BB21.

13. A method of inducing an immune response in a subject, comprising the step of administering an effective amount of the recombinant influenza B virus vector of claim 1 to a subject in need thereof.

14. The method of claim 13, wherein the influenza virus vector is administered to the subject on a plurality of occasions.

* * * * *